(12) United States Patent
Milac et al.

(10) Patent No.: US 7,553,856 B2
(45) Date of Patent: Jun. 30, 2009

(54) CRYSTALLINE FORM OF OMEPRAZOLE

(75) Inventors: Natasa H Milac, Ljubljana (SI); Anton Copar, Smartno pri Litiji (SI); Barbara Podobnik, Ljubljana (SI); Andreja C Belcic, Ljubljana (SI); Alenka Kosak, Ljubljana (SI); Brina Ornik, Ljubljana-Crnuce (SI); Uros Urleb, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 171 days.

(21) Appl. No.: 11/248,461

(22) Filed: Oct. 12, 2005

(65) Prior Publication Data

US 2006/0079560 A1 Apr. 13, 2006

Related U.S. Application Data

(63) Continuation of application No. 10/475,239, filed as application No. PCT/IB02/01350 on Apr. 24, 2002, now abandoned.

(30) Foreign Application Priority Data

Apr. 25, 2001 (SI) .............................. P-200100111

(51) Int. Cl.
*A61K 31/4439* (2006.01)
(52) U.S. Cl. .................................. 514/338; 546/273.7
(58) Field of Classification Search .............. 546/273.7; 514/338
See application file for complete search history.

(56) References Cited

U.S. PATENT DOCUMENTS

| 5,314,506 | A | 5/1994 | Midler et al. | 23/295 R |
| 6,147,103 | A | 11/2000 | Anousis et al. | 514/394 |
| 6,150,380 | A | 11/2000 | Lovqvist et al. | 514/338 |
| 6,162,816 | A | 12/2000 | Bohlin et al. | 514/338 |
| 6,268,502 | B1 | 7/2001 | Milac et al. | 546/273.7 |
| 6,627,646 | B2 * | 9/2003 | Bakale et al. | 514/322 |

FOREIGN PATENT DOCUMENTS

| EP | 0 005 129 | 10/1979 |
| WO | 98/28294 | 7/1998 |
| WO | 99/08500 | 2/1999 |
| WO | 00/02876 | 1/2000 |

OTHER PUBLICATIONS

Brittain et al., "Polymorphism in Pharmaceutical Solids", NY:Marcel Dekker, Inc., 1999, pp. 1-2, 185.*
Muzaffar et al., "Polymorphism and Drug Availability", J of Pharmacy (Lahore) (1979), 1(1), pp. 59-66.*
Taday et al., "Using Terahertz Pulse, etc.," J of Pharmaceutical Sciences, 92(4), 2003, pp. 831-838.*
Wall et al., "Pharmaceutical Applications, etc.," Pharmaceutical Manufacturing, 3(2), 1986, pp. 32-34.*
Jain et al., "Polymorphism in Pharmacy" Indian Drugs, 1986, 23(6), pp. 315-329.*
Otsuka et al., "Effect of Polymorphic Forms, etc.," Chem. Pharm. Bull. 47(6), 1999, pp. 852-856.*
Doelker et al. CA 132:325872, 2000.*
Ulicky et al., "Comprehensive Dictionary of Physical Chemistry", NY: PTR Prenctice Hall 1992, p. 21.*
Doelker, english translation of S.T.P. Pharma Pratiques (1999), 9(5), 399-409, pp. 1-33.*
Bernstein et al., "Polymorphism in Molecular Crystals", Oxford: Clarendon Press, 2002, pp. 117, 118, 272 and 273.*
Davidovich et al., "Detection of Polymorphism, etc.," American Pharmaceutical REview, IN: Russell Pub., 2004, 7(1), pp. 10, 12, 14, 16 and 100.*
Caira, "Crystalline Polymorphism of Organic Compounds", Topics in Current Chemistry, 198, Berline Heidelberg: Springer Verlag, 1998, pp. 164-208.*
CMU Pharmaceutical polymorphism, interent p. 1-3 (2002) (print out Apr. 3, 2008).*
Singhal et al., "Drug polymorphism, etc.," Advanced drug delivery reviews 56, p. 335-347 (2004).*
Rowland et al., "Clinical Pharmacokinetics, etc.," 1995, p. 123.*
Silverman, The Organic Chemistry of Drug Design and Drug Action, NY: Academic Press, 1993, 72-76.*
Doelker, english translation of Ann. Pharm. Fr. 2002, 60: 161-176, pp. 1-39.*
Ohishi et al., Structure of 5-Methoxy-2-{[4-methoxy-3,5-dimethyl-2-pyridinyl)methyl]sulfinyl}-1*H*-benzimidazole (Omeprazole), Acta Cryst., vol. C45, pp. 1921-1923 (1989).
Brittain, "Polymorphism in Pharmaceutical Solids", NY Marcel Dekker, 1999, pp. 227-263.
US Pharmacopia, 1995, pp. 1843-1844.
Halbein et al., J. Pharm. Sci., 58 (1969) pp. 911-928.

* cited by examiner

*Primary Examiner*—Patricia L Morris
(74) *Attorney, Agent, or Firm*—Luedeka, Neely & Graham, P.C.

(57) ABSTRACT

A novel crystalline form of the substrate known under the chemical name 5-methoxy-2-[[(4-methoxy-3,5-dimethyl-2-pyridinyl)methyl]sulfiny]-1H-benzimidazole, and having the generic name omeprazole, hereinafter referred to as omeprazole form C, is disclosed. Further, a process for the preparation of omeprazole form C, a pharmaceutical formulation containing omeprazole form C in admixture with pharmaceutically acceptable excipients and the use of omeprazole form C for treatment of gastrointestinal disorders are disclosed.

3 Claims, 8 Drawing Sheets

CRYSTALLINE FORM OF OMEPRAZOLE

This application is a continuation of application Ser. No. 10/475,239, filed Oct. 17, 2003 now abandoned, which is a U.S. National Phase of PCT/IB02/01350 filed Apr. 24, 2002, which claims priority to Slovenian Application No. P-200100111, filed Apr. 25, 2001; the entire disclosures of which are hereby incorporated by reference.

TECHNICAL FIELD

The invention belongs to the field of chemical technology and relates to a novel crystalline form of the substance known under the chemical name 5-methoxy-2-[[(4-methoxy-3,5-dimethyl-2-pyridinyl)methyl]sulfinyl]-1H-benzimidazole, and having the generic name omeprazole. A novel crystalline form of omeprazole disclosed herein is hereinafter referred to as omeprazole form C. Further, the invention relates to a process for the preparation of omeprazole form C with high yield and low content of impurities and residual solvents, to use of omeprazole form C for treatment of diseases related to gastric acid hypersecretion, and to a pharmaceutical composition containing the active substance omeprazole form C.

TECHNICAL PROBLEM

There is a constant need to prepare pharmaceutically stable crystalline forms of the active substance omeprazole in an industrially simple and readily feasible way with high yield and at a temperature at which the proportion of residual solvents and impurities, that is, the proportion of related substances and degradation products, is low or minimal.

PRIOR ART

The substance known under the chemical name 5-methoxy-2-[[(4-methoxy-3,5-dimethyl-2-pyridinyl)methyl]sulfinyl]-1H-benzimidazole and having the generic name omeprazole is known as a proton pump inhibitor which inhibits gastric acid secretion. Omeprazole is used for the treatment of gastric acid related diseases in mammals and especially in man.

The substance omeprazole and pharmaceutically acceptable salts thereof were described in European Patent Publication EP 5129 (Oct. 31, 1979). From the literature, two crystalline forms of omeprazole, that is, omeprazole form A and omeprazole form B are known. Form B was described by Ohishi et al., Acta Cryst. (1989), C45, 1921-1923; form A and the preparation of two crystalline forms of omeprazole were described in PCT patent publication WO 99/08500 (Feb. 25, 1999).

In PCT patent publication WO 99/08500 the described process for the preparation of omeprazole A is time-consuming e.g. 45 hours. The described synthesis is based on slow crystallization at room temperature, the basis of which is digesting (the expression digesting is understood to mean washing in such a manner when a product is suspended in a solvent in which it is insoluble or poorly, soluble and a resulting suspension is stirred for a defined time period) with alkyl alcohol, for example with methanol containing aqueous ammonia. It is generally known that the purification method, which is based on digesting, is not sufficiently effective and already to begin with requires a purer substance since washing is a surface procedure whereat it is difficult to achieve penetration of a solvent to a core, e.g., nucleus, of the crystal. In PCT patent publication WO 99/08500 it is stated that omeprazole form A exhibits better thermodynamic stability, photostability and hygroscopicity compared to previously-known omeprazole form B.

On the contrary, omeprazole form B is obtained by fast crystallization at elevated temperature. Thermal recrystallization essentially is a superior method for purification of substances to a digesting method; however, in the case of omeprazole it is not useful because omeprazole, especially in solutions at an elevated temperature rapidly disintegrates to intensely colored degradation products. Namely, omeprazole is known as an active substance which is highly sensitive to an elevated temperature. During the process of purification by thermal recrystallization, degradation products are formed which are incorporated into crystals together with a solvent each of which can have a strong impact on stability of the finished product. Besides, crystals of omeprazole form B are larger in size than crystals of form A, therefore, they may comprise both more impurities and more residual solvent than crystals of form A.

DESCRIPTION OF THE INVENTION INCLUDING EXAMPLES

A method of preparing a novel pharmaceutically stable crystalline form of the active substance omeprazole in an industrially simple and readily feasible manner, e.g., at room temperature is disclosed herein. The term pharmaceutical stability in this context includes stability of the pharmaceutical active substance under the standard conditions of testing of pharmaceutical compositions whereat the stability is evaluated by absorbance as the most sensitive method for determination of impurities, that is, related substances and degradation products.

Pharmaceutical stability depends on simultaneous influence of a variety of factors, of which the most important are the size of crystals, shape of crystals, water assay, assay of residual solvents and assay of impurities. One or more of these factors can be uniquely characterized by a process for the purification of crude omeprazole and the preparation of and isolation of the novel crystalline form of omeprazole according to the invention.

The novel form of omeprazole disclosed herein is hereinafter referred to as omeprazole form C. We have surprisingly found that apart from currently known two forms of omeprazole, form A and form B, there exists a new form hereinafter referred to as omeprazole form C, some advantages of which include a simple process for the preparation, and better yield than in case of the preparation of omeprazole form A and form B.

A process for the purification of crude omeprazole and the preparation and isolation of omeprazole form C, substantially free from other known crystalline forms of omeprazole, that is, omeprazole form A and form B, are also disclosed herein.

A crystal form of omeprazole form C has been characterized by X-ray powder analysis including data with the position of the peaks in X-ray powder diffractograms and also by the unit cell parameters. The unit cell parameters were determined by Rietveld method. Measurement using X-ray powder analysis shows that omeprazole form C is distinctly different from currently known crystalline forms of omeprazole.

Omeprazole form C, according to one embodiment of the invention, is characterized in providing an X-ray powder diffractogram pattern with substantially the following d-values.

| d-values (Å) | Relative intensity |
|---|---|
| 9.5-9.6 | very strong |
| 7.9-8.0 | strong |
| 7.4-7.5 | weak |
| 7.2 | very strong |
| 5.9-6.0 | medium |
| 5.6 | medium |
| 5.1-5.2 | very strong |
| 4.88-4.90 | weak |
| 4.81-4.84 | weak |
| 4.65-4.67 | medium |
| 4.57-4.60 | medium |
| 4.48-4.51 | strong |
| 4.34-4.36 | medium |
| 4.16-4.19 | weak |
| 3.94-3.97 | weak |
| 3.72-3.73 | strong |
| 3.58-3.59 | medium |
| 3.46-3.47 | strong |
| 3.29-3.30 | medium |
| 3.23-3.25 | strong |
| 3.19-3.20 | medium |
| 3.11-3.12 | weak |
| 3.03-3.04 | weak |

The relative intensities of d-value are identified by the following criteria:

| | |
|---|---|
| 25-100% intensity | very strong |
| 10-25% intensity | strong |
| 3-10% intensity | medium |
| 1-3% intensity | weak |

Omeprazole form C, according to another embodiment of the invention, is independently or additionally characterized by the following unit cell parameters in the range of:

| a(Å) | b(Å) | c(Å) | α(°) | β(°) | γ(°) |
|---|---|---|---|---|---|
| 9.705-9.740 | 10.335-10.375 | 10.525-10.590 | 90.95-91.15 | 111.70-111.90 | 116.25-116.50 |

Omeprazole form C according to another embodiment of the invention, is independently or additionally characterized by Fourier Transform Infrared Spectroscopy (FT IR). Omeprazole form C has the characteristic absorption bands at substantially the following wavelengths:

$1204$ $cm^{-1}$, $1076$ $cm^{-1}$, $1024$ $cm^{-1}$, $1014$ $cm^{-1}$, $822$ $cm^{-1}$

The new crystalline form of omeprazole, according to another embodiment of the invention, is independently or additionally characterized by the ratio of the intensities of the absorption bands of FT IR analysis at the wavelengths 1120 $cm^{-1}$ in 1112 $cm^{-1}$, which differ from currently known crystalline forms of omeprazole, forms A and B:

| OMEPRAZOLE FORM | THE RATIO BETWEEN THE INTENSITY OF ABSORPTION BANDS AT 1120 $cm^{-1}$ TO 1112 $cm^{-1}$ |
|---|---|
| A | from 1:4.5 to 1:5.5 |
| B | from 1:1.0 to 1:1.9 |
| C | from 1:2.1 to 1:3.0 |

A process for the purification of crude omeprazole and the preparation and isolation of the stable form C, substantially free from other known crystalline forms of omeprazole, that is, omeprazole form A and form B is also disclosed herein. Its is generally known that crystals of active omeprazole substance containing a large amount of solvent and different impurities are less stable than pure omeprazole crystals irrespective of the shape of crystals. Therefore, also disclosed herein is a method to prepare such crystals of omeprazole form C characterized by one or more of:

low or minimal amount of residual solvents,
low or minimal amount of related substances,
low or minimal amount of degradation products and
high or maximal yield of the target compound.

A process for the preparation of omeprazole form C, according to one embodiment of the invention, comprises the following two steps:

a) Recrystallization by precipitation (e.g., fast crystallization at room temperature),
b) Digesting of the crystals in water.

Omeprazole form C can be prepared by dissolving crude omeprazole, obtained in the reaction between 5-methoxy-2-[[(4-methoxy-3,5-dimethyl-2-pyridinyl)methyl]thio]-1H-benzimidazole and 3-chloroperoxybenzoic acid at room temperature first in a solvent or a mixture of solvents in which omeprazole is freely soluble and, thereafter, omeprazole form C is precipitated at room temperature with a solvent in which it is poorly soluble. By this process pure crystals of omeprazole are precipitated while impurities remain in solution. The precipitated crystals are filtered off and washed. The yield can be increased by cooling crystal suspension before filtration to a temperature in the range of –10 to –20° C. For dissolving of omeprazole, suitable solvents include: 40% aqueous methylamine; a mixture of 40% aqueous methylamine with dichloromethane, chloroform or acetone; a mixture of 25% ammonia with dichloromethane, chloroform or acetone; and a mixture triethylamine with dichloromethane, chloroform or acetone. Preferably a mixture of 40% aqueous methylamine and acetone, is used. The precipitating solvent, preferably comprises acetone.

One advantage of the above method—recrystallization by precipitation is that a substance containing one or more impurities, especially degradation products, can be used as the starting substance. Further, recrystallization by precipitation is also advantageous because it can be carried out at room temperature at which the potential for subsequent formation of degradation products of omeprazole is reduced. Further, its advantage is that in a single step two problems can be solved: to prepare a stable substance according to the process with a high or maximum possible yield and simultaneously to efficiently purify a substance (from starting materials side products and degradation products) comprising a larger starting amount of impurities, especially degradation products.

Upon completing a procedure of recrystallization by precipitation the assay of residual solvents decreased. The product obtained is then suspended in water, e.g., at room temperature, followed by agitating with a mixer making strong turbulence, for example an ULTRA-TURRAX® mixer (type 18/10, Janke&Kunkel), from 30 minutes to 1 hour, e.g., at room temperature. The product formed is then filtered off, washed with water, and dried in vacuo at room temperature to constant weight.

Omeprazole form C, obtained by a process disclosed herein, can contain less than 200 µg/g of acetone as a residual solvent, e.g., determined by gas chromatography, preferably less than 100 µg/g of acetone. By practice of a method disclosed herein an active substance is obtained which is stable according to the standard protocol for characterization of stability of a pharmaceutical active substance.

Omeprazole form C, obtained by a process disclosed herein, can be substantially free from other known crystal forms of omeprazole, that is, omeprazole form A or form B.

It is known that stability of an active substance depends on upon residual solvents and on present impurities—related substances and degradation products. The stability of omeprazole samples was determined by a standard procedure for testing the substances in pharmaceutical industry (CPMP/ICH/2736/99). Packaged omeprazole samples were aged for a definite period of time (1 month, 3 months, 6 months) under stress condition of aging (at a temperature 40° C. and 75% relative humidity which is a standard accelerated condition for stability testing of pharmaceutical formulations) and/or accelerated condition of aging (at a temperature 25° C. and 60% relative humidity which is a standard accelerated condition for stability testing of pharmaceutical active substances). Determination of absorbance, measured according to Ph Eur method (PhEur 3 Suppl 2000), is used as the criterion for evaluation of the sample quality during stability testing. It previously has been shown that measurement of absorbance is a more sensitive method for monitoring the process of omeprazole decomposition than, for example, detection of present impurities using chromatographic methods (PhEur 3 Suppl 2000).

Omeprazole form C, according to the invention, is a proton pump inhibitor and can be used for the control of gastric acid secretion in mammals and especially in man. It inhibits the enzyme $H^+/K^+$-ATPase in the parietal cell, thus, it also inhibits the last phase of acid secretion. Consequently, both basal and stimulated acid secretion irrespective of the stimulus can be reduced. Omeprazole form C can be used in the treatment of duodenal ulcer, gastric ulcer, reflux esophagitis and Zollinger-Ellison syndrome.

The preparation of a pharmaceutical composition containing omeprazole form C and pharmaceutically acceptable excipients is also disclosed herein. The pharmaceutical composition is suitable for different routes of administration such as oral, parenteral, transdermal, etc. A suitable pharmaceutical form can be, for example, a capsule, tablet, dispersion, solution, suspension, emulsion, gel, powder, etc. A suitable quantity of the medicament is within the range of 10 mg to 80 mg daily, preferably between 20 mg and 40 mg of total daily dosage.

The invention is illustrated but in no way limited by the following Examples:

EXAMPLE 1

Process for the Preparation of Omeprazole Form C from Crude Omeprazole by Precipitation with Acetone from a Mixture of Aqueous Solution of Methylamine 125 g of crude omeprazole, obtained by oxidation of 5-methoxy-2-[[(4-methoxy-3,5-dimethyl-2-pyridinyl)methyl]thio]-1H-benzimidazole with 3-chloroperoxybenzoic acid, were dissolved while stirring in a mixture of 100 ml of 40% of aqueous methylamine and 125 ml of acetone at room temperature. To this clear solution was added 2000 ml of acetone, the combined solution was stirred for 1 hour at room temperature, and thereafter cooled to a temperature in the range of −10 to −15° C. The product formed was filtered off and then washed with acetone. The crystals formed still wet were suspended in 400 ml of water at room temperature and thereafter stirred vigorously for 1 hour while cooling to a temperature not exceeding 20° C. with an ULTRA-TURRAX® mixer (type 18/10, Janke&Kunkel). The product obtained—omeprazole form C was filtered off, washed with water, and dried in vacuo at room temperature to constant weight.

Yield: 98.7 g (79%).

EXAMPLE 2

Process for the Preparation of Omeprazole Form C from Crude Omeprazole by Precipitation with Acetone from a Mixture of Aqueous Solution of Methylamine and Dichloromethane 125 g of omeprazole, obtained by oxidation with 5-methoxy-2-[[(4-methoxy-3,5-dimethyl-2-pyridinyl)methyl]thio]-1H-benzimidazole with 3-chloroperoxybenzoic acid, were dissolved while stirring in a mixture of 62.5 ml of 40% of methylamine and 125 ml of dichloromethane at room temperature. To this clear solution was added 2000 ml of acetone, the combined solution was stirred for 1 hour at room temperature and thereafter cooled to a temperature in the range of −10 to −15° C. The product formed was filtered off, washed with acetone and dried in vacuo at room temperature to constant weight. Yield: 103.7 g (83%).

The crystals formed were suspended in 400 ml of water at room temperature and thereafter stirred vigorously for 1 hour while cooling to a temperature not exceeding 20° C. with an ULTRA-TURRAX® mixer (type 18/10, Janke&Kunkel). The product obtained—omeprazole form C—was filtered off, washed with water, and dried in vacuo at room temperature to constant weight.

Yield: 102.7 g (99%).

EXAMPLE 3

Characterization of Omeprazole Form C by X-ray Powder Analysis

Figure 1:
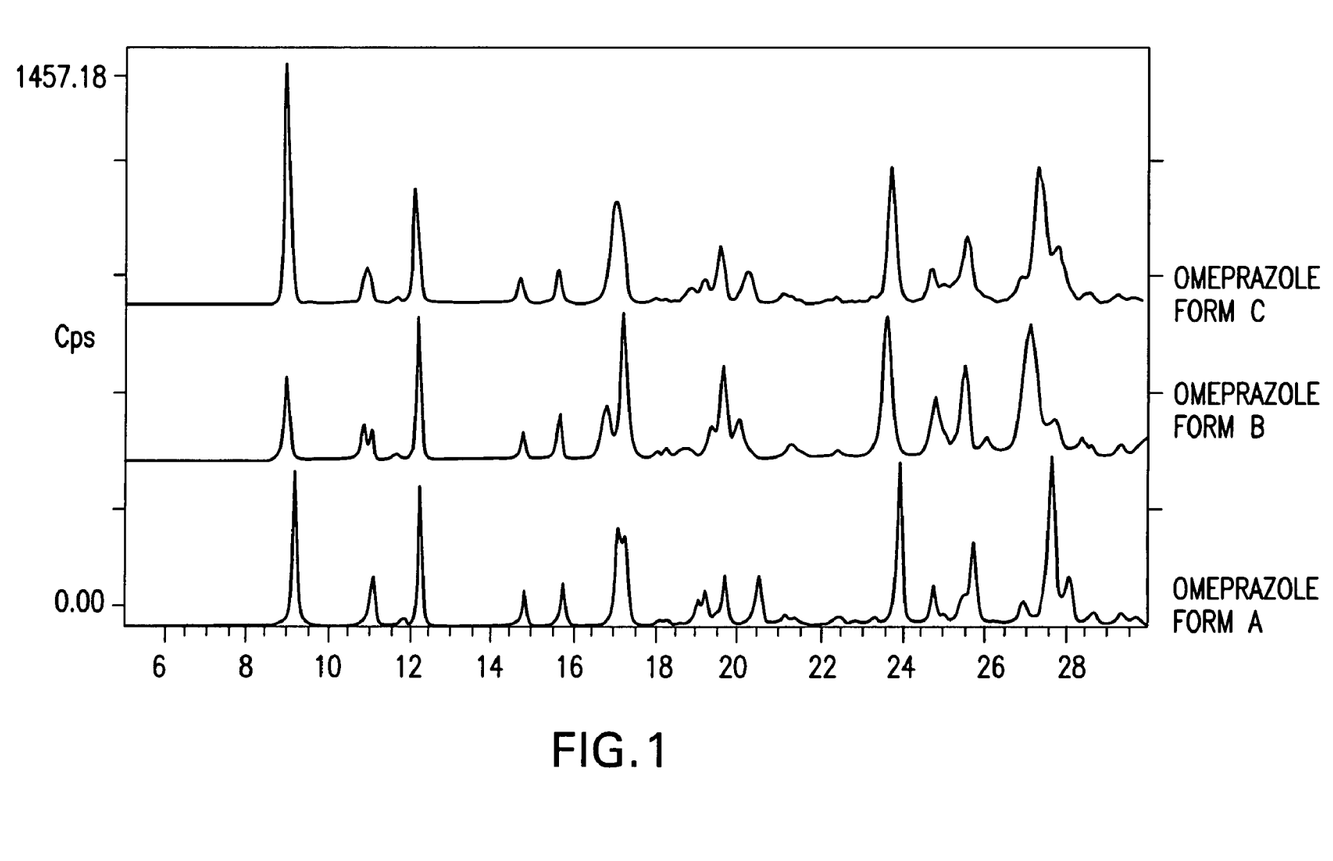
FIG. 1: an X-ray powder diffractogram of omeprazole forms A, B and C.

FIG. 1 is the X-ray powder diffractogram of the following samples:
  omeprazole form A, synthesized according to Example 1 disclosed in PCT patent publication WO 99/08500;
  omeprazole form B, synthesized according to Example 2 disclosed in PCT patent publication WO 99/08500; and
  omeprazole form C, synthesized according to hereinabove disclosed Example 1.

The X-ray powder diffractograms were recorded on a Siemens D-500 X-ray Diffractometer (Bragg-Brentano reflectance geometry) with CuKα radiation within the angle range 5 to 30° 2θ, with a 0.02° step and an integration time 10 seconds. Variable slits were adjusted to 6 mm sample illumination, and entrance slit to 0.2 mm.

Table 1 lists the d-values characterized by X-ray powder analysis of the novel crystalline form of omeprazole—omeprazole form C—synthesized according to hereinabove disclosed Example 1, and for comparison d-values of form A and form B, as disclosed in PCT patent publication WO 99/08500. The positions of the peaks (d-values) of omeprazole form C were determined according to the standard procedure (Kug&Aleksander, L. E. (1974)).

| 25-100% intensity | very strong |
| 10-25% intensity | strong |
| 3-10% intensity | medium |
| 1-3% intensity | weak |

From the above data it is evident that omeprazole form C is a novel crystalline form of omeprazole.

Table 2 lists the unit cell parameters of the novel crystalline form of omeprazole—omeprazole form C—synthesized according to hereinabove disclosed Example 1, and for comparison the unit cell parameters of omeprazole form A and form B as disclosed in PCT patent publication WO 99/08500. The unit cell parameters of omeprazole form C were calculated using Rietveld comparison.

TABLE 2

Unit cell parameters of omeprazole forms A, B and C

| | UNIT CELL PARAMETERS | | | | | |
|---|---|---|---|---|---|---|
| FORM | a(Å) | b(Å) | c(Å) | α(°) | β(°) | γ(°) |
| A | 9.729(4) | 10.410(4) | 10.468(3) | 90.77(3) | 111.51(3) | 116.78(3) |
| B | 9.694(10) | 10.257(10) | 10.717(6) | 91.76(7) | 112.14(7) | 115.56(5) |
| C | 9.705-9.740 | 10.335-10.375 | 10.525-10.590 | 90.95-91.15 | 111.70-111.90 | 116.25-116.50 |

TABLE 1 d-values of omeprazole form C, form A and form B

| FORM C d-values (Å) | relative intensity | FORM A d-values (Å) | relative intensity | FORM B d-values (Å) | relative intensity |
|---|---|---|---|---|---|
| 9.5-9.6 | very strong | 9.5 | very strong | 9.6 | very strong |
| 7.9-8.0 | strong | 7.9 | strong | 8.0 | medium |
| 7.4-7.5 | weak | 7.4 | weak | 7.9 | medium |
| 7.2 | very strong | 7.2 | very strong | 7.5 | weak |
| 5.9-6.0 | medium | 6.0 | medium | 7.1 | very strong |
| 5.6 | medium | 5.6 | strong | 5.9 | medium |
| 5.1-5.2 | very strong | 5.2 | strong | 5.6 | medium |
| 4.88-4.90 | weak | 5.1 | strong | 5.3 | strong |
| 4.81-4.84 | weak | 4.89 | weak | 5.1 | strong |
| 4.65-4.67 | medium | 4.64 | medium | 4.54 | medium |
| 4.57-4.60 | medium | 4.60 | medium | 4.48 | strong |
| 4.48-4.51 | strong | 4.53 | weak | 4.41 | medium |
| 4.34-4.36 | medium | 4.49 | medium | 4.14 | weak |
| 4.16-4.19 | weak | 4.31 | medium | 3.75 | strong |
| 3.94-3.97 | weak | 4.19 | weak | 3.57 | medium |
| 3.72-3.73 | strong | 4.15 | weak | 3.47 | strong |
| 3.58-3.59 | medium | 3.95 | weak | 3.40 | weak |
| 3.46-3.47 | strong | 3.71 | strong | 3.28 | strong |
| 3.29-3.30 | medium | 3.59 | medium | 3.22 | medium |
| 3.23-3.25 | strong | 3.48 | medium | 3.02 | weak |
| 3.19-3.20 | medium | 3.45 | strong | | |
| 3.11-3.12 | weak | 3.31 | weak | | |
| 3.03-3.04 | weak | 3.22 | strong | | |
| | | 3.17 | medium | | |
| | | 3.11 | weak | | |
| | | 3.04 | weak | | |
| | | 3.00 | weak | | |

The relative intensities of d-value were identified by the following criteria:

From the above data it is evident that omeprazole form C is a novel crystalline form of omeprazole.

EXAMPLE 4

Characterization of Omeprazole Form C Using Fourier Transform Infrared Spectroscopy (FT IR)

A crystal structure of omeprazole form C, synthesized according to hereinabove disclosed Example 1, was characterized using Fourier Transform Infrared Spectroscopy (FT IR). For comparison, FT IR spectra of omeprazole form A and form B, synthesized according to Examples 1 and 2 of PTC patent publication WO 99/08500, were also recorded.

Analysis of the samples was performed on a Nicolet Nexus, DTGS KBr detector. In the analysis a diffuse reflectance measurement technique (DRIFTS=Diffuse Reflectance Infrared Fourier Transform Spectroscopy) and an insert for Nexus Smart Collector measurements were used. The samples without prior treatment were mixed with KBr (IR purity level—concentration 50 weight % of omeprazole to KBr (IR grade). All spectra were measured with 64 scans, that is, the number of replicate measurements within single measurement, at resolution 2 $cm^{-1}$.

Figure 2:
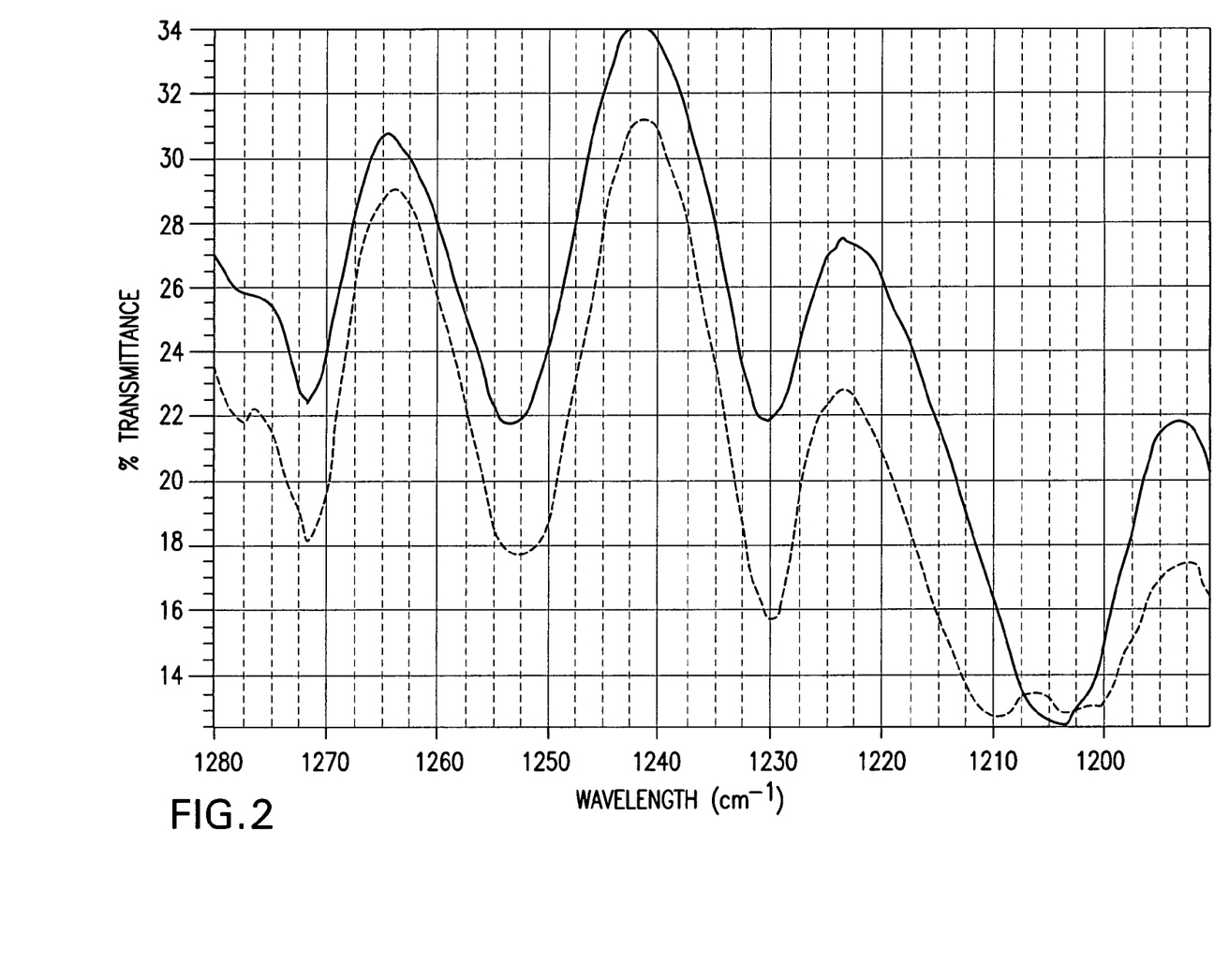
FIGS. 2 to 4: FT IR spectra of omeprazole form A (dashed line) and omeprazole form C (solid line).
Figure 3:
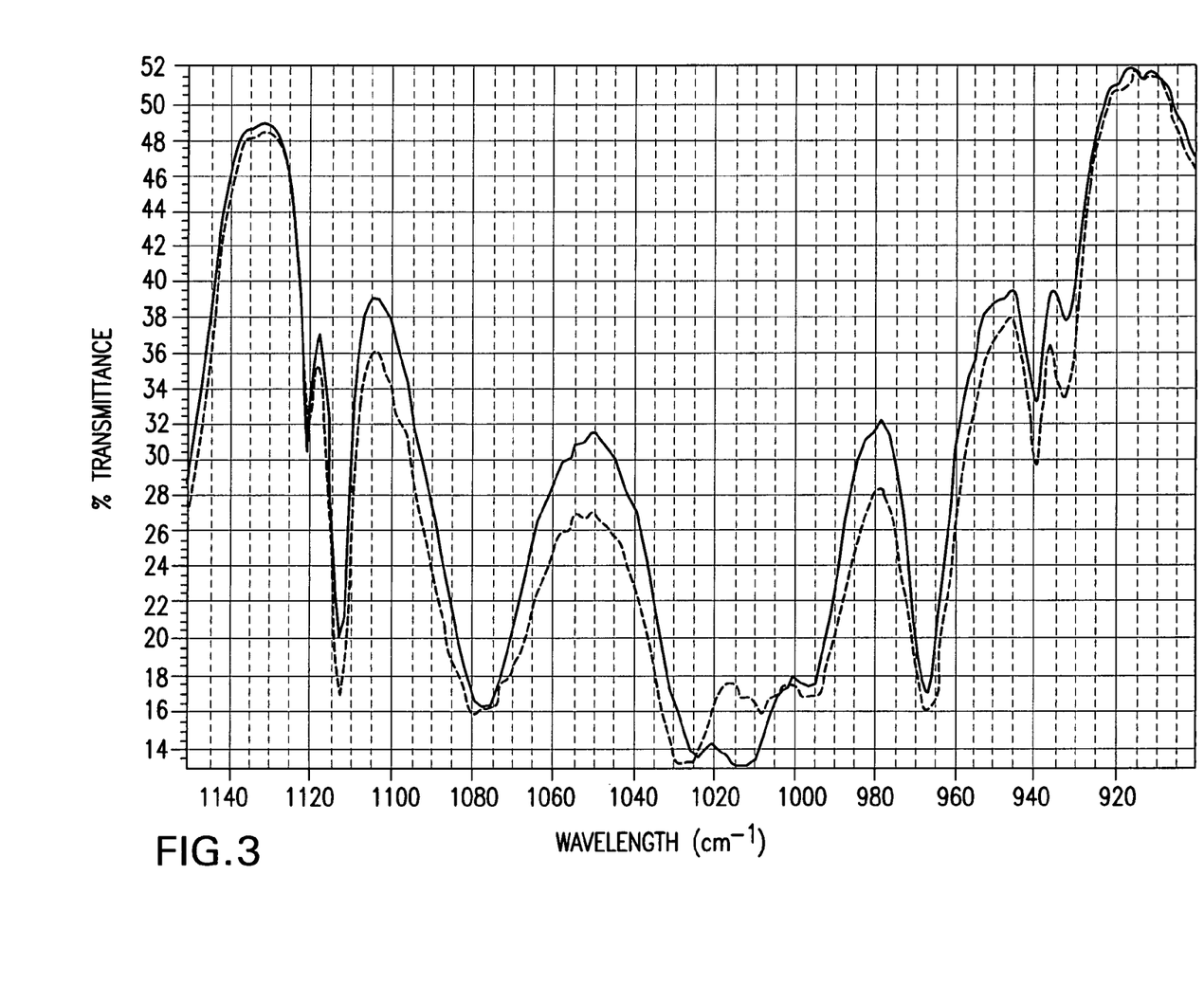
Figure 4:
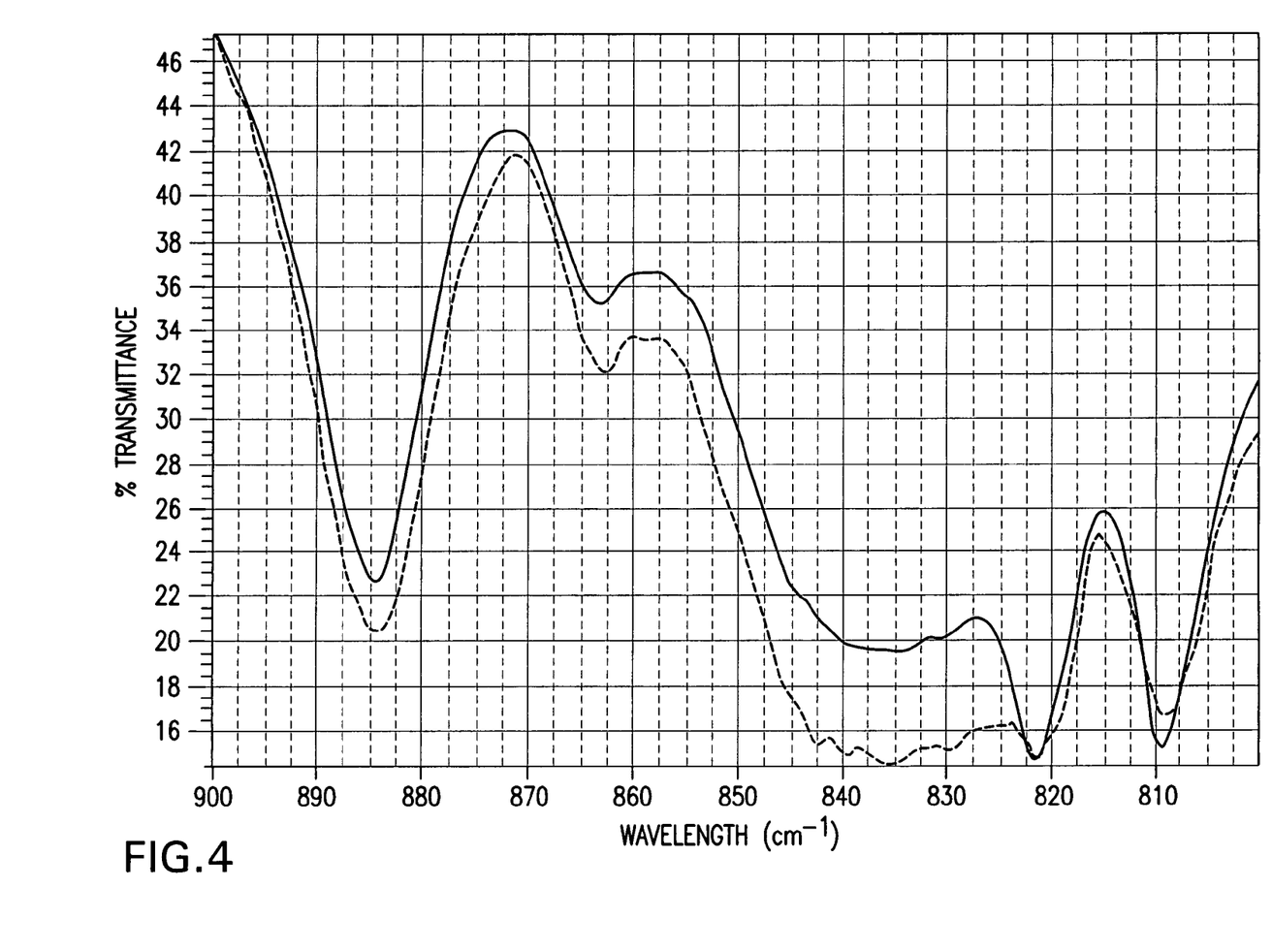

FIGS. 2 to 4: FT IR spectra of omeprazole form A (dashed line) and omeprazole form C (solid line).

Figure 5:
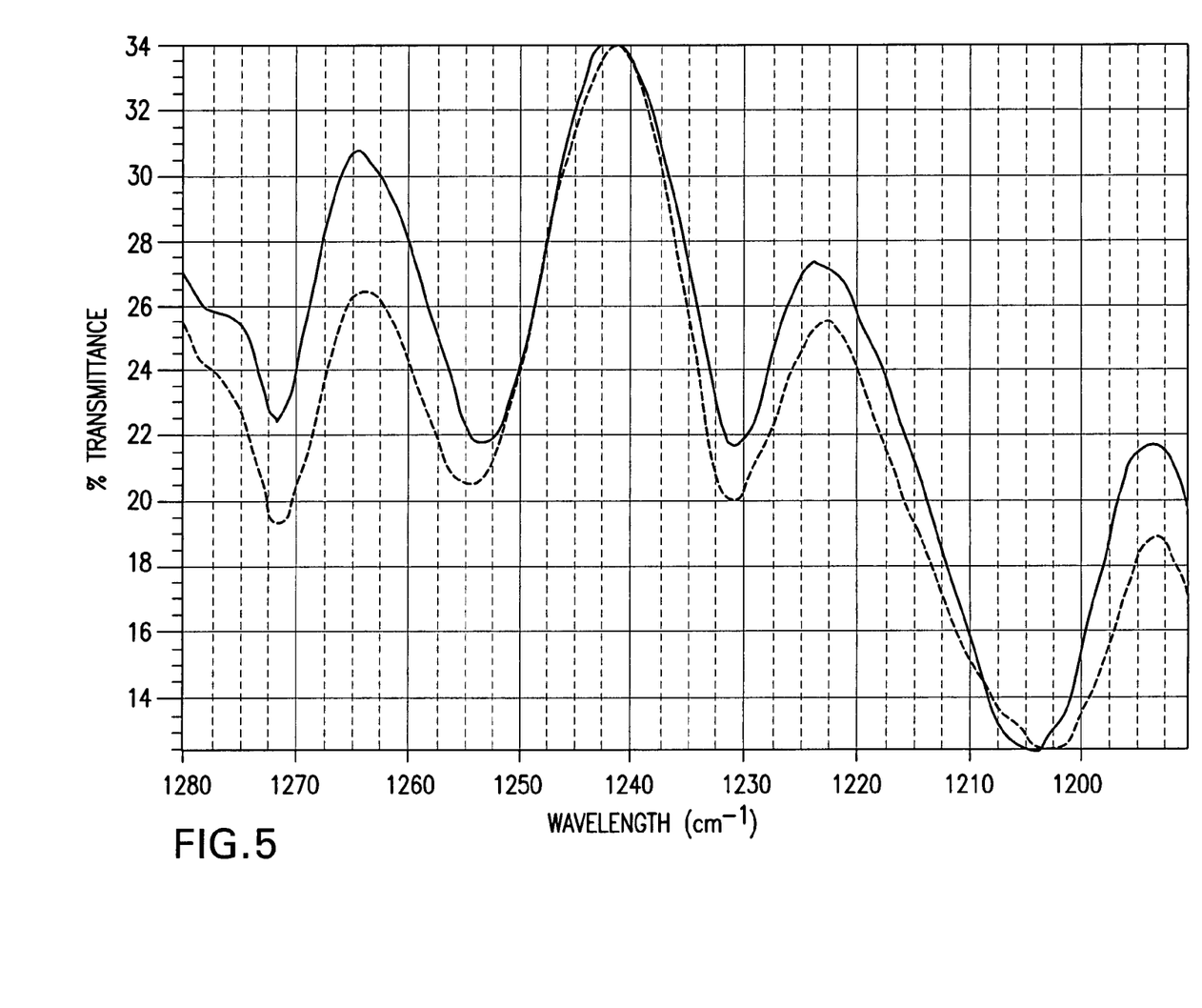
FIGS. 5 to 7: FT IR spectra of omeprazole form B (dashed line) and omeprazole form C (solid line).
Figure 6:
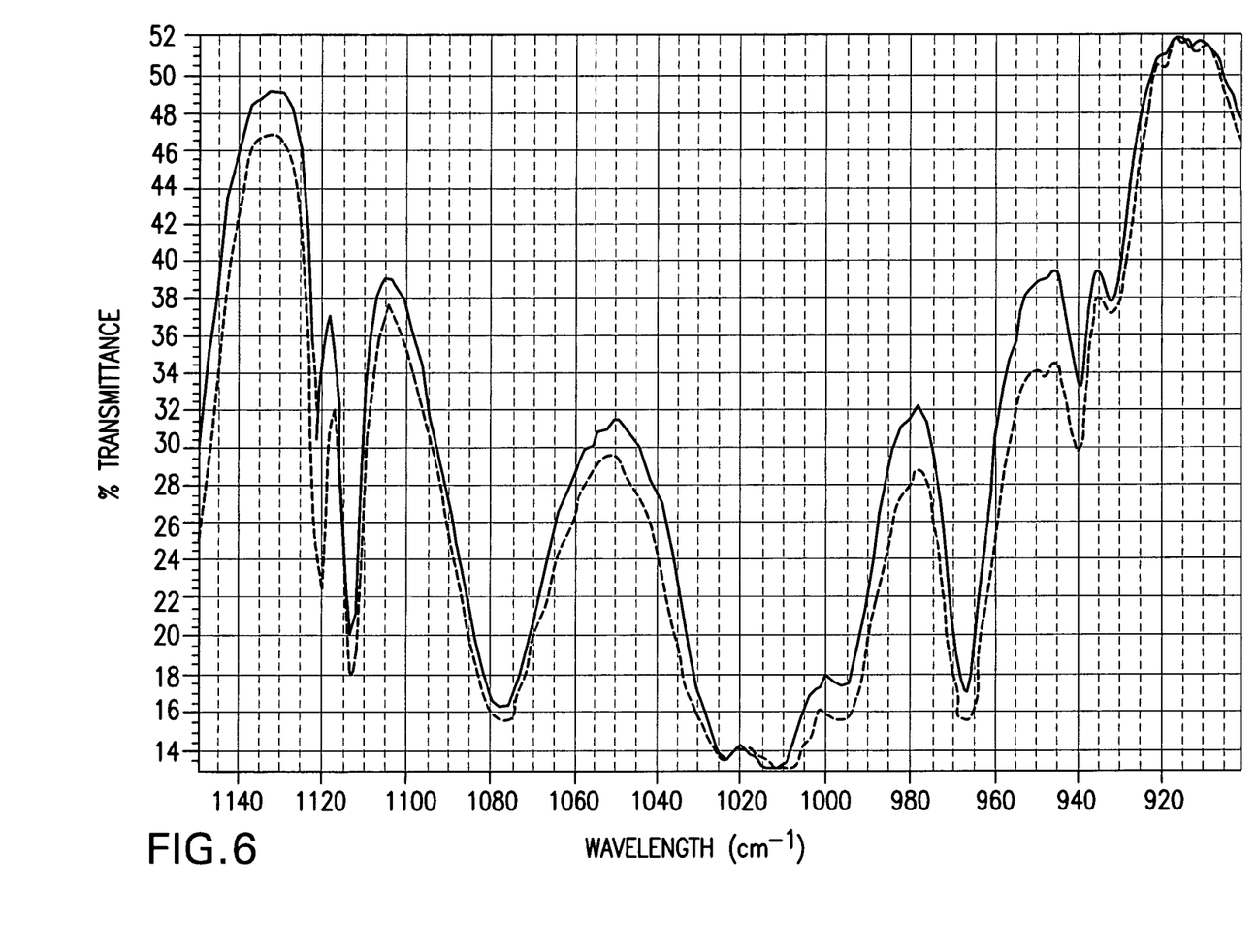
Figure 7:
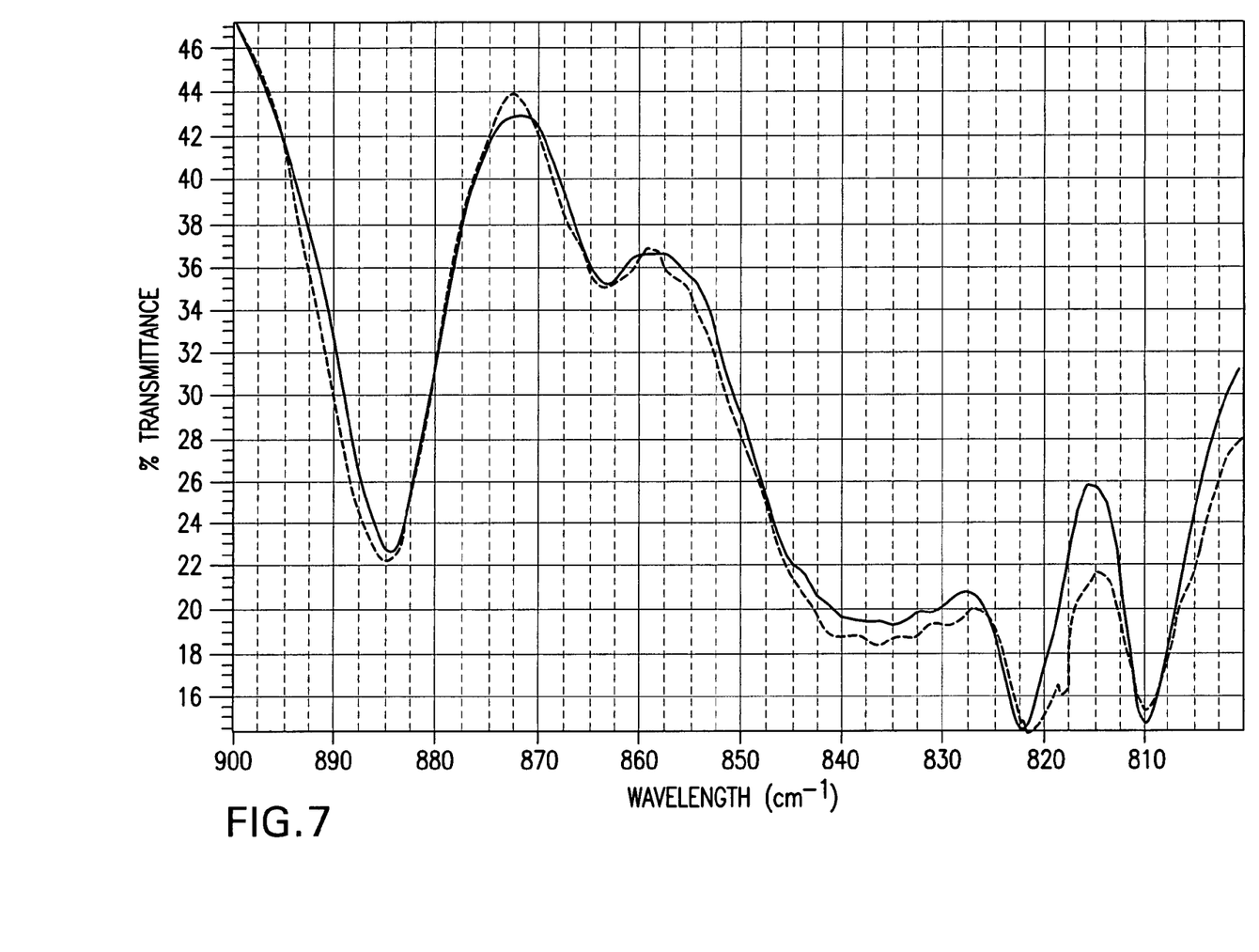

FIGS. 5 to 7: FT IR spectra of omeprazole form B (dashed line) and omeprazole form C (solid line).

As it is evident from FIGS. 2 to 4, the sample of omeprazole form A exhibits characteristic absorption bands at the following wavelengths:

1210 $cm^{-1}$, 1201 $cm^{-1}$, 1079 $cm^{-1}$, 1075 $cm^{-1}$, 1029 $cm^{-1}$, 1025 $cm^{-1}$, 1013 $cm^{-1}$, 1008 $cm^{-1}$.

As it is evident from FIGS. 5 to 7, the sample of omeprazole form B exhibits characteristic absorption bands at the following wavelengths:

1202 cm$^{-1}$, 1025 cm$^{-1}$, 1020 cm$^{-1}$, 1011 cm$^{-1}$, 1008 cm$^{-1}$, 821 cm$^{-1}$.

As it is evident from FIG. 2 to 7, the sample of omeprazole form C exhibits characteristic absorption bands at substantially the following wavelengths:
1204 cm$^{-1}$, 1076 cm$^{-1}$, 1024 cm$^{-1}$, 1014 cm$^{-1}$, 822 cm$^{-1}$.

The characteristic absorption bands of omeprazole form C do not overlap the characteristic absorption bands of omeprazole form A and form B.

The crystalline forms of omeprazole, forms A, B and C, can be independently or additionally distinguished by the ratio of the intensities of the absorption bands at wavelengths 1120 cm$^{-1}$ and 1112 cm$^{-1}$, being the highest for omeprazole form A and lowest for omeprazole form B.

TABLE 3

The ratio between the intensity of the absorption bands at wavelengths 1120 cm$^{-1}$ and 1112 cm$^{-1}$ depending on the crystalline form of omeprazole

| FORM | THE RATIO BETWEEN THE INTENSITY OF THE ABSORPTION BANDS AT 1120 cm$^{-1}$ TO 1112 cm$^{-1}$ |
|---|---|
| A | from 1:4.5 to 1:5.5 |
| B | from 1:1.0 to 1:1.9 |
| C | from 1:2.1 to 1:3.0 |

Figure 8:
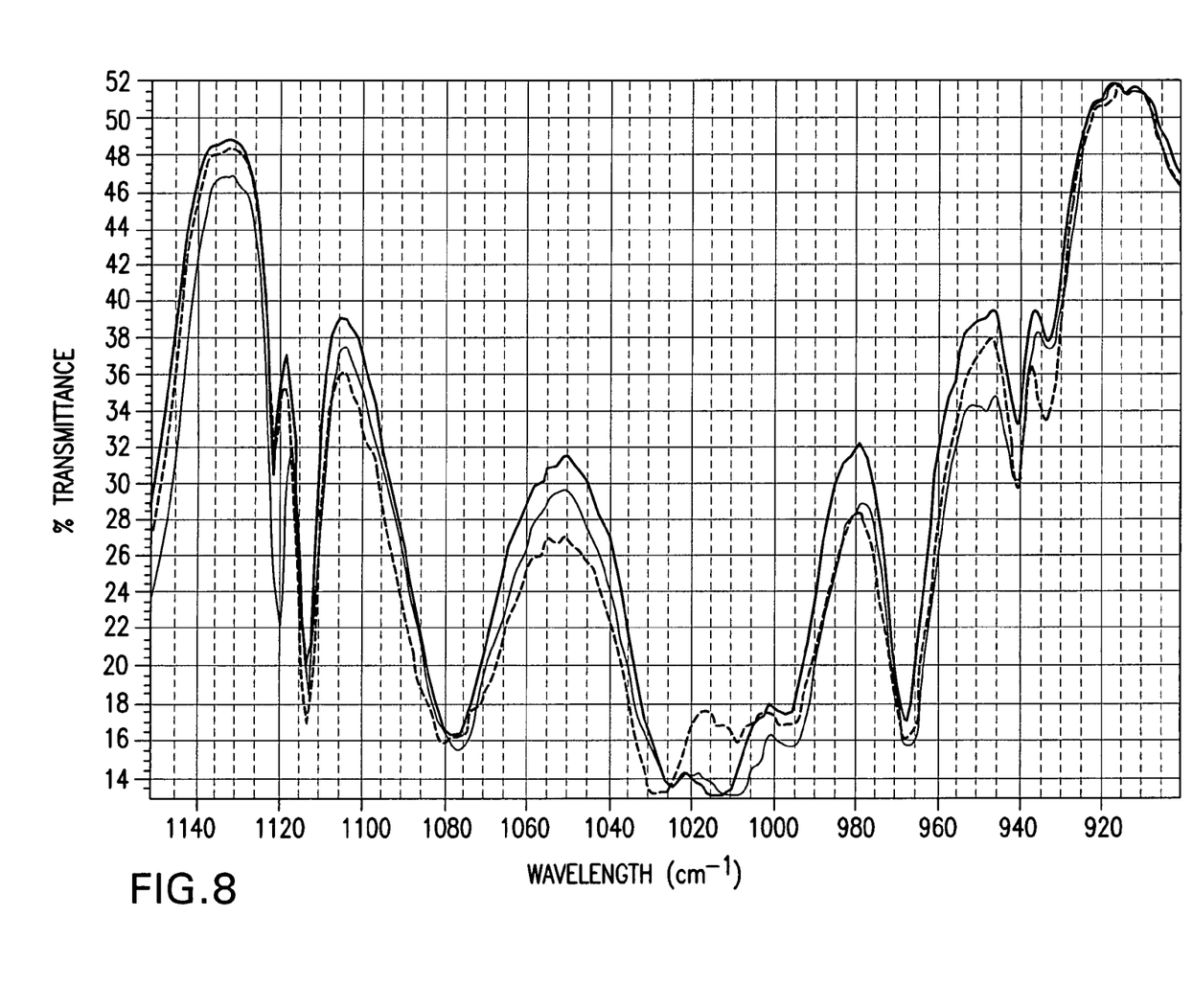
FIG. 8: FT IR spectra of omeprazole form A (dashed line), omeprazole form B (dotted line) and omeprazole form C (solid line) within the wavelength range 1120 $cm^{-1}$ and 1112 $cm^{-1}$ wherein the ratios of intensities of absorption bands differentiate for omeprazole form A, form B and form C.

FIG. 8: FT IR spectra of omeprazole form A (dashed line), omeprazole form B (dotted line) and omeprazole form C (solid line) including the range of wavelengths 1120 cm$^{-1}$ and 1112 cm$^{-1}$, where the ratios of the intensities of the absorption bands of omeprazole form A, form B and form C differ.

EXAMPLE 5

Pharmaceutical Formulation a) Pellet Cores

Composition for 1000 g of Pellet Cores:

| | |
|---|---|
| Omeprazole form C | 100 g |
| Low-substituted hydroxypropylcellulose (13 to 16% of hydroxypropoxyl groups) | 150 g |
| Microcrystalline cellulose | 150 g |
| Mannitol | 478 g |
| Croscarmellose sodium | 50 g |
| Polyvinylpyrrolidone K 25 | 70 g |
| Polyoxyethylated hydrogenated castor oil | 2 g |

Prior to use, the pharmaceutically acceptable excipients used were dried in such a manner to provide loss on drying less than 1.0%, preferably less than 0.5% of total weight of each individual pharmaceutically acceptable excipient.

The batch of 1000 g of pellet cores was prepared according to the following procedure:

2 g of polyoxyethylated hydrogenated castor oil (Cremophor® RH 40) were dissolved in 300 g of absolute ethanol at room temperature. The solution formed (302 g) was sprayed on a previously prepared blend of powder components of 100 g of omeprazole form C, obtained according to the procedure described Example 1, 150 g of dried low-substituted hydroxypropylcellulose (L-HPC LH-20), 150 g of dried microcrystalline cellulose, 478 g of dried mannitol, 50 g of dried croscarmellose sodium and 70 g of dried polyvinylpyrrolidone K 25 in a fluid bed granulator at room temperature. The resulting wet mass was extruded and spheronized. The pellet cores formed were dried in a fluid bed or chamber dryer at inlet air temperature of 35 to 45° C. to loss on drying not less than 0.5% of total weight of pellet cores.

1000 g of pellet cores were obtained.

b) Enteric Coated Pellets

| | |
|---|---|
| Pellet cores | 1000 g |
| Hypromellose phthalate | 150 g |
| Dibutyl sebacate | 15 g |

150 g of hypromellose phthalate and 15 g of dibutyl sebacate were dissolved in a mixture of 1754 g of absolute ethanol and 438 g of acetone at room temperature. The resulting solution was sprayed onto the pellet cores in the fluid-bed device.

c) Encapsulating

The produced enteric coated pellets were filled into gelatin or cellulose capsules to provide an assay of omeprazole 20 mg/capsule on a capsule filling machine.

The invention claimed is:

1. 5-Methoxy-2-[[(4-methoxy-3,5-dimethyl-2-pyridnyl)methyl]sulfinyl]-1H-benzimidazole form C, characterized in providing an X-ray powder diffraction pattern exhibiting substantially the following d-values:

| d-values (Å) | Relative intensity |
|---|---|
| 9.5-9.6 | very strong |
| 7.9-8.0 | strong |
| 7.4-7.5 | weak |
| 7.2 | very strong |
| 5.9-6.0 | medium |
| 5.6 | medium |
| 5.1-5.2 | very strong |
| 4.88-4.90 | weak |
| 4.81-4.84 | weak |
| 4.65-4.67 | medium |
| 4.57-4.60 | medium |
| 4.48-4.51 | strong |
| 4.34-4.36 | medium |
| 4.16-4.19 | weak |
| 3.94-3.97 | weak |
| 3.72-3.73 | strong |
| 3.58-3.59 | medium |
| 3.46-3.47 | strong |
| 3.29-3.30 | medium |
| 3.23-3.25 | strong |
| 3.19-3.20 | medium |
| 3.11-3.12 | weak |
| 3.03-3.04 | weak. |

2. 5-Methoxy-2-[[(4-methoxy-3,5-dimethyl-2-pyridnyl)methyl]sulfinyl]-1H-benzimidazole form C, according to claim 1, characterized by having the following unit cell parameters: a=9.705-9.740Å, b=10.335-10.375Å, c=10.525-10.590Å, α=90.95-91.15°, β=111.70-111.90°, γ=116.25-116.50°.

3. 5-Methoxy-2-[[(4-methoxy-3,5-dimethyl-2-pyridnyl)methyl]sulfinyl]-1H-benzimidazole form C, characterized in comprising characteristic absorption bands by Fourier Transform Infrared Spectroscopy at the wavelengths 1204 cm$^{-1}$, 1076 cm$^{-1}$, 1024 cm$^{-1}$, 1014 cm$^{-1}$ and 822 cm$^{-1}$.

* * * * *